United States Patent [19]

Guire

[11] Patent Number: 4,973,493
[45] Date of Patent: Nov. 27, 1990

[54] METHOD OF IMPROVING THE BIOCOMPATIBILITY OF SOLID SURFACES

[75] Inventor: Patrick E. Guire, Eden Prairie, Minn.

[73] Assignee: Bio-Metric Systems, Inc., Eden Prairie, Minn.

[21] Appl. No.: 108,765

[22] Filed: Oct. 15, 1987

Related U.S. Application Data

[63] Continuation-in-part of Ser. No. 428,074, Sep. 29, 1982, Pat. No. 4,722,906, and Ser. No. 920,567, Oct. 17, 1986, abandoned.

[51] Int. Cl.$^5$ .................... A01N 1/02; A61K 1/02; A61F 2/54
[52] U.S. Cl. ........................... 427/2; 623/66; 623/901; 435/181; 436/905
[58] Field of Search ............... 623/1, 6, 11, 66, 901; 427/2; 435/181; 436/532, 525, 905

[56] References Cited

U.S. PATENT DOCUMENTS

| | | | |
|---|---|---|---|
| 3,808,113 | 4/1974 | Okamura et al. | 204/159.12 |
| 3,826,678 | 7/1974 | Hoffman et al. | 117/81 |
| 3,955,012 | 5/1976 | Okamura et al. | 427/2 |
| 3,959,078 | 5/1976 | Guire | 195/63 |
| 4,007,089 | 2/1977 | Smith, III | 195/68 |
| 4,240,163 | 12/1980 | Galin | 3/13 |
| 4,311,573 | 1/1982 | Mayhan et al. | 204/159.15 |
| 4,378,224 | 3/1983 | Nimni et al. | 8/94 |
| 4,378,435 | 3/1983 | Takagi et al. | 435/180 |
| 4,419,444 | 12/1983 | Quash | 435/7 |
| 4,434,150 | 2/1984 | Azad et al. | 424/1.1 |
| 4,451,568 | 5/1984 | Schneider et al. | 435/181 |
| 4,500,676 | 2/1985 | Balazs et al. | 525/54.2 |
| 4,526,714 | 7/1985 | Feijen et al. | 260/112 |
| 4,526,909 | 7/1985 | Urist | 523/115 |
| 4,530,974 | 7/1985 | Munro et al. | 525/329.4 |
| 4,536,179 | 8/1985 | Anderson et al. | 604/266 |
| 4,589,881 | 5/1986 | Pierschbacher | 623/11 |
| 4,589,964 | 5/1986 | Mayhan et al. | 522/85 |
| 4,595,632 | 6/1986 | Mayhan et al. | 428/409 |
| 4,605,413 | 8/1986 | Urry et al. | |
| 4,663,233 | 5/1987 | Beavers | 428/412 |
| 4,687,808 | 8/1987 | Jarrett et al. | |
| 4,715,858 | 12/1987 | Lindstrom | 623/5 |
| 4,716,122 | 12/1987 | Scheefers | 436/532 |
| 4,722,906 | 2/1988 | Guire | 436/501 |
| 4,828,563 | 5/1989 | Müller-Lierheim | 623/66 |

OTHER PUBLICATIONS

Price list from Biotechnology Research Enterprises, S.A. Pty. Ltd., dated Nov., 1985, entitled "Photobiotin Acetate".

P. Guire et al., "Photochemical Coupling of Enzymes to Mammalian Cells", Pharmacological Research Communications, vol. 9:131–141, (1977).

P. Guire et al., "Stepwise-Cross-linking Reagents for Photocoupling of Enzymes and Lectins to Mammalian Cells", Glycoconjugate Research, vol. II:1051–1054, (1979).

P. Guire, "Stepwise Thermophotochemical Cross-linking for Enzyme Stabilization and Immobilization", Enzyme Engineering, vol. 3:63–70, (1978).

P. Guire, "Photochemical Immobilization of Enzymes and Other Biochemicals", Methods in Enzymology, vol. XLIV:280–288, (ed. Klaus Mosbach 1976).

Ebert et al., "The Anticoagulant Activity of Derivatized and Immobilized Heparins", Biomaterials: Interfacial Phenomena and Applications, Cooper et al., Eds. Am. Chem. Soc., pp. 161–176, (1982).

Larsson et al., "Covalent Binding of Proteins to Grafted Plastic Surfaces Suitable for Immunoassays", 98 J. Immuno. Methods, 129–135, (1987).

Engbers et al., "An In Vitro Study of the Adhesion of Blood Platelets onto Vascular Catheters. Part I.", 21 Journal of Biomedical Materials Research, pp. 613–627, (1987).

Evangelista et al., "Coating of Two Polyether-polyurethanes and Polyetheylene with a Heparin-Poly-(Vinyl Alcohol) Hydrogel", 7 Biomaterials, pp. 206–211, (1986).

Heyman et al., "Heparinized Polyurethanes: In Vitro and In Vivo Studies", 19 Journal of Biomedical Materials Research, pp. 419–436, (1985).

Palatianos et al., "Extracorporeal Left Ventricular Assistance with Prostacyclin and Heparinized Centrifugal Pump", 35 The Annals of Thoracic Surgery, pp. 504–515, (1983).

Larm et al., "A New Non-Thrombogenic Surface Prepared by Selective Covalent Binding of Heparin Via a Modified Reducing Terminal Residue", 11 Biomat. Med. Dev. Art. Org., pp. 161–173, (1983).

Hoffman et al., "A New Method for Covalent Coupling of Heparin and Other Glycosaminoglycans to Substances Containing Primary Amino Group", 117 Carbohydrate Research, pp. 328–331, (1983).

(List continued on next page.)

Primary Examiner—Randall L. Green
Assistant Examiner—Paul Prebilic
Attorney, Agent, or Firm—James R. Haller; Bauman, Mary P.; Gregory P. Kaihoi

[57] ABSTRACT

A method for modifying the solid surface to improve its biocompatibility is disclosed. The method employs molecules of a biocompatible agent and a chemical linking moiety possessing a photochemically reactive group capable upon activation of covalently bonding to the solid surface and possessing a different reactive group as capable upon activation of covalently bonding to separate molecules of the biocompatible agent. The method comprises applying stimulus to sequentially activate the groups and covalently bind the different reactive group of the linking moiety to the molecules of the biocompatible agent and to photochemically covalently bind the linking moiety to the solid surface with a sufficient population density to enable the molecules of the biocompatible agent to effectively shield the solid surface and to provide a biocompatible surface.

15 Claims, No Drawings

OTHER PUBLICATIONS

Bennegard et al., "Material Thrombogenicity in Central Venous Catheterization: I. A Comparison Between Uncoated and Heparin-coated. Long Antebrachial, Polyethylene Catheters", 26 Acta Anaesth. Scand., pp. 112–120, (1982).

Nilsson et al., "Polargraphic $pO_2$ Sensors with Heparinized Membranes for In Vitro and Continuous In Vivo Registration", 41 Scan. J. Clin. Lab. Invest., pp. 557–563, (1981).

Kim et al. "Surface Modification of Polymers for Improved Blood Compatibility", 1 CRC Critical Reviews in Biocompatibility, pp. 229–260, (Issue 3).

METHOD OF IMPROVING THE BIOCOMPATIBILITY OF SOLID SURFACES

This application is a continuation-in-part of U.S. Patent Application Ser. No 428,074, filed Sept. 29, 1982 now U.S. Pat. No. 4,727,906, and U.S. Patent Application Ser. No. 920,567, filed Oct. 17, 1986 now abandoned.

FIELD OF INVENTION

This invention relates to the field of biochemistry and particularly to the enhancement of the biocompatibility of various surfaces.

BACKGROUND OF THE INVENTION

The implantation of such biomaterial articles as substitute blood vessels, synthetic and intraocular lenses, electrodes, catheters and the like in and onto the body is a rapidly developing area of medicine. A primary impediment to the long term use of such biomaterial implantables as synthetic vascular grafts has been the lack of satisfactory graft surfaces. The uncoated surfaces of synthetic blood vessels made from plastics, for example, often stimulate rapid thrombogenic action. Various plasma proteins play a role in initiating platelet and fibrin deposition on plastic surfaces. These actions lead to vascular constriction to hinder blood flow, and the inflammatory reaction that follows can lead to the loss of function of the synthetic implantable.

A "biomaterial" may be defined as a material that is substantially insoluble in body fluids and that is designed and constructed to be placed in or onto the body or to contact fluid of the body. Vascular grafts and contact lenses are examples of biomaterials.

Ideally, a biomaterial will have the following characteristics:

1. It will not induce undesirable reactions in the body such as blood clotting, tissue death, tumor formation, allergic reaction, foreign body reaction (rejection) or inflammatory reaction.
2. It will have the physical properties such as strength, elasticity, permeability and flexibility required to function as intended.
3. It can be purified, fabricated and sterilized easily.
4. It will substantially maintain its physical properties and function during the time that it remains implanted in or in contact with the body, whether it be an hour or a lifetime.

As used herein, the solid surface of a biomaterial is characterized as "biocompatible" if it is capable of functioning or existing in contact with biological fluid and/or tissue of a living organism with a net beneficial effect on the living organism. Long term biocompatibility is desired for the purpose of reducing disturbance of the host organism.

A number of approaches have been suggested to improve the biocompatibility of implantable items. One approach has been to modify the surface of a biomaterial to prevent undesirable protein adhesion by providing the biomaterial with a low polarity surface, a negatively charged surface or a surface coated with biological materials such as enzymes, endothelial cells and proteins. Solid surfaces have been coated with biochemical materials such as heparin, albumin and streptokinase to enhance thromboresistance. Albumin in particular has been physically adsorbed onto and electrostatically and covalently bound to polymer surfaces.

Munro, et. al, U.S. Pat. No. 4,530,974 discloses a method of adsorbing albumin to a water-insoluble polymer such as polyurethane by covalently binding to the surface a nonionic hydrophobic aliphatic chain to which albumin will selectively bind.

Nimni et al, U.S. Pat. No. 4,378,224 teaches a method of coating animal tissues, used to make prosthetic devices, through the formation of a three dimensional cross linked matrix primarily composed of a calcification inhibitor.

An example of an adverse reaction that is caused by the presence of a biomaterial is the deposition of protein on contact lenses. Often contact lens wearers develop an intolerance to their contact lenses with time and this intolerance may be linked to irritation and allergic responses to biochemicals (proteins, lipids, mucopolysaccharides, and others) which deposit onto the lenses while they are worn. Current cleansing and disinfection procedures remove some of these deposits, but these procedures often leave holes and crevices in the lenses which add to the eye irritation of the wearer and serve as foci for further biochemical deposition.

Guire, U.S. Pat. No. 3,959,078, describes the use of reagents to covalently bind an enzyme to aminoethyl cellulose or alkylamine glass. See, also: Guire, *Stepwise Thermophotochemical Cross linking for Enzyme Stabilization and Immobilization*; Enzyme Engineering 3:63 70 1978) and Guire, *Photochemical Immobilization of Enzymes and Other Biochemicals*, Methods in Enzymology XLIV:280–288 (1976). These references describe a process of covalently binding an enzyme to substrates such as chemical derivatives of controlled-pore glass, cellulose, agarose and polyacrylamides by thermochemically coupling a linking reagent to the solid surface and photochemically coupling the enzyme to the linking reagent to provide a surface useful in the performance of in vitro diagnostic assays.

SUMMARY OF THE INVENTION

The invention relates to biomaterials that are provided with desired biocompatible surfaces. A method for modifying the solid surface of a biomaterial employs molecules of a biocompatible agent and a chemical linking moiety possessing a photochemically reactive group capable, upon activation, of covalently bonding to the solid surface and possessing different reactive group that is capable, upon activation, of covalently bonding to separate molecules of the biocompatible agent. One of the groups is unresponsive to activation by a stimulus to which the other group is responsive. The method comprises applying stimulus to sequentially activate the groups to covalently bind the different reactive group of the linking moiety to the molecules of the biocompatible agent and to photochemically covalently bind the linking moiety to the solid surface with a sufficient population density to enable the molecules of the biocompatible agent to effectively shield the solid surface and to provide a biocompatible effective surface.

A biocompatible "effective" surface is thus formed of a plurality of separate molecules of a biocompatible agent covalently linked, through a linking moiety, to the solid surface of a biomaterial to provide that surface with substantially the same biocompatible characteristics as are possessed by the biocompatible agent. The effective surface formed by the molecules of the biocompatible agent need not cover the entire surface of a biomaterial. It may cover the surface in spots. For example, spots along the surface of vascular grafts may be covered by a cell attachment factor such as fibronectin. The biocompatible effective surface formed at those spots then act as foci for attachment of cells to the modified surface.

In one embodiment, a method of the invention is used to selectively attach molecules of a biocompatible agent to a solid surface. The method uses a chemical linking moiety possessing: (1) a photochemically reactive group capable, upon activation of covalently bonding to the solid surface; (2) a selector group forming a member of a specific binding pair of which the other member is a receptor carried by the molecule of the biocompatible agent; and (3) a different reactive group that is sterically distinct from the selector group and is capable, upon activation, of covalently bonding to separate molecules of the biocompatible agent. The method comprises the steps of attaching the chemical linking moiety to the solid surface by activating the photochemically active group to form a covalent bond with the solid surface, with a sufficient population density to enable the molecules of the biocompatible agent to effectively shield the solid surface when bound to provide a biocompatible effective surface, reacting the selector group with the receptor carried by the biocompatible agent to bring the different reactive group into covalent bonding proximity with the biocompatible agent and then activating the different reactive group to form a covalent linkage to the biocompatible agent.

The different reactive group of the linking moiety desirably is a thermochemical group or a photochemical group that is unresponsive to the stimulus to which the first mentioned photochemically reactive group responds and to which molecules of the biocompatible agent will covalently bind.

In another embodiment of the invention there is provided a device having a biocompatible effective surface formed of separate molecules of a biocompatible agent covalently linked by a chemical linking moiety residue to the solid surface of the device. The chemical linking moiety residue includes a residue of a photochemically reactive group covalently bonded to the solid surface, and, covalently bonded to molecules of the biocompatible agent, the residue of a different reactive group, one of the reactive groups being unresponsive to a stimulus to which the other reactive group responds. The individual molecules of the biocompatible agent are attached through the linking moiety residue to the solid surface sufficiently proximate to one another as to cause said molecules to effectively shield the solid surface and to provide a biocompatible effective surface.

The biocompatible agent is chosen to enhance the function of a particular device. For example, the function of contact lenses may be enhanced by attaching molecules of polyethylene glycol to the lens surfaces to diminish the deposition of proteins on these surfaces. As another example, a cell attachment factor such as fibronectin or laminin may be bonded to a device having a polyvinyl chloride surface to increase cell attachment to the device. This is desirable in the case of implantables such as catheters and substitute blood vessels.

Yet another embodiment of the invention involves a method for modifying the solid surface of a biomaterial, the method employing molecules of a biocompatible agent joined to one another to form a biocompatible film, and a chemical linking moiety capable of linking the film to the solid surface of the biomaterial. The chemical linking moiety includes a photochemically reactive group capable upon activation of covalently bonding to the solid surface, and the residue of a reactive group covalently bonded to the film (e.g., to the residue of the biocompatible agent molecules making up the film). One of the reactive groups is unresponsive to a stimulus to which the other reactive group responds. The method comprises activating the photochemically reactive group with a stimulus to covalently bind the biocompatible molecules. By "joined" in this context, reference is made not only to covalent bonding of adjacent biocompatible agent molecules but also to interactions caused b such forces as hydrogen bonding, ionic bonding, bonding through Van der Waals forces, and the like.

The biocompatible agent having molecules joined to one another to form a film may comprise molecules of one agent or it may comprise molecules of two or more agents such as heparin and albumin.

DESCRIPTION OF THE PREFERRED EMBODIMENTS

The solid surface that is rendered biocompatible in accordance with the invention desirably is of a synthetic or natural material that is insoluble in physiological fluids. The surface may be one or more surfaces of devices intended to function in contact with tissue and/or fluids of living organisms. The solid surface of the device may be any suitable metal such as polished titanium or stainless steel or a polymer such as polyurethane, polyvinylpyrrolidone, silicone elastomers, polyethylene, polytetrafluoroethylene, poly (p-phenyleneterephthalamide), polyvinyl chloride, polypropylene, polyolefins, polyesters. polyacrylates (including polymethacrylates); minerals or ceramics such as hydroxyapitite; human tissue such as bone, skin and teeth; organic materials such as wood, cellulose and compressed carbon; and other natural and synthetic materials such as glass, rubber, wood and the like. Examples of devices which may be provided with biocompatible surfaces in accordance with this invention include vascular graft tubing, dialysis tubing or membrane, blood oxygenator tubing or membrane, ultrafiltration membrane, intra aortic balloon, blood bag, catheter, suture, soft or hard tissue prosthesis, synthetic prosthesis, artificial organs, and lenses for the eye such as contact and intraocular lenses.

The solid surface is desirably thermochemically unreactive. "Thermochemically unreactive" means that the surface is free of any surface treatment designed to increase the ability of the surface to thermochemically react. Examples of thermochemically unreactive surfaces include polytetrafluroethylene, polyethylene, polypropylene, polyvinyl chloride, polyvinylpyrrolidone, silicone elastomers, stainless steel and titanium.

Molecules of a biocompatible agent are attached to the surfaces of biomaterials to improve biocompatibility. The biocompatible agent may be a growth factor such as endothelial cell growth factor, epithial cell growth factor, osteoblast growth factor, fibroblast growth factor, platelet derived growth factor, neural growth factor, or angiogenin growth factor; an antimicrobial agent such as lysosyme or penicillin; an antithrombogenic agent such as heparin, albumin, streptokinase, tissue plasminogin activator (TPA) or urokinase; a thrombogenic agent such as collagen or a hydrophilic polymer such as polyethylene glycol (a synthetic polymer), hyluronic acid, chitosan or methyl cellulose, and other proteins, carbohydrates and fatty acids. The biocompatible agent may comprise molecules of one of the above listed agents or it may comprise molecules of two or more agents. For example, the biocompatible agent may comprise molecules of both albumin and heparin.

In one embodiment the molecules of a biocompatible material are joined to one another to form a film that is attached to a solid surface by a linking moiety. The biocompatible agent desirably may be hyaluronic acid or albumin. A biocompatible device having a film attached may be an artificial hip joint coated with a film of hyaluronic acid.

The chemical linking moiety preferably has the formula A—X—B in which A represents a photochemically reactive group capable in response to specific activation of bonding covalently to a solid surface; B represents a different reactive group capable desirably in response to specific activation to which group A is unresponsive, of forming a covalent bond to a biocompatible agent and X represents a relatively inert, noninterfering skeletal moiety joining groups "A", and "B", that is resistant to cleavage in aqueous physiological fluid. The physiological fluid referred to is such fluid with which X will come in contact. In a method of the invention group "A" of the linking moiety is covalently bound to the solid surface, with a sufficient population density to enable the molecules of the biocompatible agent to effectively shield the solid surface when the molecules are covalently bound to group "B" to provide a biocompatible effective surface. A biocompatible device of this invention has a solid surface to which molecules of a biocompatible agent has been bound via the chemical-linking moiety as follows: solid surface-A residue-X—B residue-molecules of a biocompatible agent.

In one embodiment the molecules of the biocompatible agent are selectively bound to the solid surface with a sufficient population density to provide a biocompatible effective surface using a chemically linking moiety that has the formula:

in which R represents a selector group that is a member of a specific bonding pair and that is reactive to form a bond with a receptor forming the other member of the specific binding pair and carried by a selected biocompatible agent and A, and B represent the groups described above as A and B. X represents a relatively inert, non-interfering skeletal radical joining groups "A", "B" and "R" and sterically enabling group "B" to separate from group "R" by at least about 10 Å.

Groups "B" and "R" are sterically distinct groups; that is, they may, during the course of thermal vibration and rotation separate by a distance of at least 10 Å. Group R, a "selector" group, representing a member of a specific binding pair, commonly forms a bond, usually noncovalent, with the biocompatible agent at an epitopic or other binding site of the latter (which site typifies a "receptor" herein). The group "B", which upon activation can covalently bond to the biocompatible agent, may be sterically spaced from the group "R", thereby enabling the covalent bond to be formed at a site spaced from the receptor site. In turn, the selector receptor bond may be disassociated from the receptor site through breakage of a fragile bond between the selector group and the chemical linking moiety followed by removal of the selector by, e.g., dialysis, environmental changes (pH, ionic strength, temperature, solvent polarity, etc.) or through spontaneous catalytic modification of the selector group (as when the biocompatible agent is an enzyme), etc. The receptor thus is reactivated to permit subsequent reaction with members of the specific binding pair.

As referred to herein, "specific binding pair" refers to pairs of substances having a specific binding affinity for one another. Such substances include antigens and their antibodies, haptens and their antibodies, enzymes and their binding partners (including cofactors, inhibitors and chemical moieties whose reaction the enzymes promote), hormones and their receptors, specific carbohydrate groups and lectins, vitamins and their receptors, antibiotics and their antibodies and naturally occuring binding proteins, etc. The concept of employing specific binding pairs in analytical chemistry is well known and requires little further explanation. Reference is made to Adams, U.S. Pat. No. 4,039,652, Maggio, et al, U.S. Pat. No. 4,233,402 and Murray, et al, U.S. Pat. No. 4,307,071, the teachings of which are incorporated by reference herein.

X is preferably a $C_1$–$C_{10}$ alkyl group such as polymethylene, a carbohydrate such as polymethylol, a polyoxyethylene, such as polyethylene glycol or a polypeptide such as polylysine.

The reactive group B is a group that upon suitable activation covalently bonds to proteinaceous or other biocompatible agents. Such groups are typified by thermochemical groups and photochemical groups, as described and exemplified in Guire, U.S. Pat. No. 3,959,078, the teachings of which are incorporated herein by reference.

The photochemically reactive groups (A) (the covalent bonding of which is activated by actinic radiation) may be typified by aryl, alkyl and acyl azides, oxazidines, isocyanates (nitrene generators), alkyl and 2 ketodiazo derivatives and diazirines (carbene generators), aromatic ketones (triplet oxygen generators), aromatic diazonium derivatives and numerous classes of carbonium ion and radical generators. Reference is made to Frederick J. Darfler and Andrew M. Tometsko, chapter 2 of *Chemistry and Biochemistry of Amino Acids, Peptides and Proteins* (Boris Weinstein, ed) vol. 5, Marcel Dekker, Inc. New York, 1978, for further description of photochemically reactive groups. Azidonitrophenyls, fluoroazido nitrobenzenes, and aromatic ketones form a preferred group due to their stability to chemical reaction conditions in the dark and their susceptibility to activation by light of wave lengths harmless to most biomaterials, to form short-lived reactive intermediates capable of forming covalent bonds in useful yield with most sites on the biomaterial.

Nitrophenylazide derivatives (shown as including the X group) appropriate for use as photochemically reactive groups for the most part can be derived from fluoro-2-nitro-4-azidobenzene, and include 4-azido-2-nitrophenyl(ANP)-4-aminobutyryl, ANP-6-aminocaproyl, ANP-11-aminoundecanoyl, ANP-glycyl, ANP-aminopropyl, ANP-mercaptoethylamino, ANP-diaminohexyl, ANP-diaminopropyl, and ANP-polyethylene glycol. ANP-6-aminocaproyl, ANP-11-aminoundecanoyl, and ANP-polyethylene glycol are preferred. Aromatic ketones preferred for use as photochemically reactive groups include benzylbenzoyl and nitrobenzylbenzoyl.

Thermochemical reactive groups (that are activated by heat energy) are typified by and include nitrophenylhalides, alkylamino, alkylcarboxyl, alkylthiol, alkylaldehyde, alkylmethylimidate, alkylisocyanate, alkylisothiocyanate and alkylhalide groups.

Groups appropriate for use as thermochemically reactive groups include carboxyl groups, hydroxyl groups, primary amino groups, thiol groups, maleimides and halide groups. N-oxysuccinimide carboxylic esters of such groups as 6-amino hexanoic acid and amino undecanoic acid, alkylthiol groups such as mercaptosuccinic anhydride and beta-mercaptopropionic acid, homocysteinethiolactones, and polyetheylene glycol derivatives are preferred.

The devices of this invention have biocompatible solid surfaces that include molecules of a biocompatible agent and a chemical linking moiety residue. The chemical linking moiety residue possesses a residue of a photochemically reactive group bonded to the solid surface and possesses a residue of a different reactive group covalently bonded to the biocompatible agent. The residue of the photochemically reactive group is that portion of a photoreactive group (described above) represented by "A" in the general formula, that remains after a covalent bond has formed. When the photoreactive group is ANP and the solid substrate is polyethylene, the residue is a carbon-nitrogen bond. A nitrene formed when ANP is light activated, reacts with a carbon of the polyethylene to form a covalent bond. When the photoreactive group is BBA and the solid substrate is polyethylene, the residue is a carbon carbon bond. When BBA is stimulated by light, the carbon joining the two phenyl groups is activated to a triplet state causing a carbon-carbon bond to form between the polyetheylene and the BBA and to form an hydroxyl group. When the different reactive group ("B") is NOS the residue is the carboxyl carbon of that group bonded to an oxygen or nitrogen group of a biocompatible agent such as fibronectin.

As enzymes, cell attachment factors and certain other substances that may be employed as biocompatible agents are somewhat sensitive to high temperatures, it is desired that the different reactive group on the linking moiety employed in the present invention be activated by (that is, undergo covalent bonding in response to) easily applied and nonharmful stimuli such as moderate heat (e.g., body temperature or below) and light. Reactive groups that are unresponsive to the stimulus to which the photochemically reactive group responds may be groups that react to changes in pH, or to the addition of another chemical species and the like.

The chemical linking moieties desirably covalently bond to the surface in such population to enable the molecules of biocompatible agent moieties to shield the solid surface and to provide a biocompatible effective surface. The density of bound chemical moieties necessary to provide an effective surface varies with the particular biocompatible agent used.

The invention ma be better understood by reference to the following non limiting examples. Table 1 is a list of abbreviations of terms used in the following descriptions.

TABLE 1

| LIST OF ABBREVIATIONS | |
| --- | --- |
| Abbreviation | Full Name |
| EGF | Endothelial growth factor |
| PEG | Polyethylene glycol |

TABLE 1-continued

| LIST OF ABBREVIATIONS | |
| --- | --- |
| Abbreviation | Full Name |
| PVC | Polyvinyl chloride |
| PE | Polyethylene |
| PP | Polypropylene |
| PTFE | Polytetrafluoroethylene |
| FNAB | Fluoronitroazidobenzene |
| ANP | 4-azido-2-nitrophenyl |
| KOH | Potassium hydroxide |
| TLC | Thin layer chromatography |
| NOS | N-oxysuccinimide |
| EAC(A) | Epsilon amino caproic acid |
| AUD(A) | Amino undecanoic acid |
| BBA | Benzoyl benzoic acid |
| DMSO | Dimethyl sulfoxide |
| DMF | Dimethylformamide |
| EDC | 1-ethyl-3-(3-dimethylaminopropyl) carbodimide |
| PEG-1000 | Polyethylene glycol, molecular weight 1000 |
| PEG-4000 | Polyethylene glycol molecular weight 4000 |
| PBS | Phosphate buffered saline |
| FN | Fibronectin |
| COL | Collagen |
| nBBA | Nitrobenzoylbenzoic acid |
| HEPES | N-2-hydroxyethylpiperazine - N'-2-ethane sulfonic acid |
| HSA | Human serum albumin |
| HGG | Human gamma globulin |
| LYZ | Lyzosyme |
| mmole | millimole |
| ml. | milliliter |
| $MW_{app}$ | Approximate molecular weight |
| mg | milligram |
| M | Molar |
| pmole | picamole |
| ng | nanogram |
| ug | microgram |
| ID | Inner diameter |

EXAMPLE 1

Endothelial Cell Attachment/Growth

1. Plastic Surfaces.

Various cell factors were coupled to polymeric surfaces tested in vitro to determine the effect of these factors upon cell attachment and overgrowth. The polymeric surfaces included polyvinyl chloride (PVC), polyethylene (PE), polypropylene (PP) and polytetrafluoroethylene (PTFE) GORE-TEX (6 mm reinforced expanded PTFE, a trademarked product of W. L. Gore and Associates, Inc.). Commercial tubing tested included polyester (Dacron, D, 6 mm straight knitted dacron velour, a trademarked product of Dupont), silicone elastomer, (Silastic ®, S, 0.03 I.D., tubing, a trademarked product of Dow Corning) and polyurethane. Polystyrene plates were used as controls.

2. Preparation of the Chemical Linking Moiety.

The chemical linking moiety used in these examples were the N oxysuccinimide (NOS) esters of 4-azido2-nitrophenyl epsilon amino caproic acid (ANP-EACA), 4-azido-2-nitro phenyl amino undecanoic acid (ANP AUDA) and benzoylbenzoic acid (BBA). ANP-EAC-NOS and ANP AUD NOS were prepared by the method described in P. Guire, D. Fliger and J. Hodgson, "Photochemical Coupling of Enzymes to Mammalian Cells", *Pharmacological Research Communications*, Vol. 9, pp 131-141 (1977), incorporated herein by reference. Briefly, fluoro-2-nitro-4-azido benzene was reacted with either epsilon amino caproic acid or amino undecanoic acid to substitute the relatively poorly reactive fluoride with an amino alkyl carboxy group. The carboxy group was then esterified, by carbodiimide activation with N hydroxy succinimide to yield the N-oxysuccinimide carboxylic ester. The NOS ester of benzoylbenzoic acid was prepared by esterifying the carboxy group by carbodiimide activation with N-hydroxy succinimide.

When ANP-EAC-NOS or ANP-AUD-NOS is the chemical linking moiety used, the ANP group is the photochemically reactive group represented by the letter "A" in the A—X—B general formula discussed above. The NOS group is the different reactive group represented by the letter "B" in the formula. The EAC or AUD group acts as the spacer between the two reactive groups and is represented by the X in the general formula. When BBA-NOS is the chemical linking moiety, the benzoylbenzoic group is the photochemically reactive group represented by the "A" in the general formula and the NOS group is the different reactive group represented by the letter "B". The group represented by X is the carbon connecting the two reactive groups.

3. Covalent Bonding of Growth Factors to the Chemical Linking Moieties.

The biocompatible agents fibronectin, laminin, collagen, endothelial growth factor, and human serum albumin were tested for their abilities to promote endothelial cell attachment and overgrowth on synthetic biomaterials. These agents were coupled to the N-oxysuccinimide (NOS) esters of 4-azido-2-nitrophenyl epsilon amino caproic acid (ANP-EACA), 4-azido-2-nitrophenyl-undecanoic amino acid (ANP-AUDA) or benzoylbenzoic acid (BBA) as follows. As used herein "photolabeled" refers to a biocompatible agent that has been coupled to a chemical linking moiety by the different reactive group and that has a photochemically reactive group.

A. Covalent Binding of Fibronectin and Laminin to the Linking Moiety.

Human fibronectin (University of Wisconsin Medical School) and mouse laminin (obtained from Bethesda Research Lab.) were separately dissolved at 1 mg/ml concentrations in 0.1M borate, pH 9.0. A solution of ANP-EAC-NOS in dry dimethylformamide ("DMF"), ANP-AUD-NOS in dry DMF, or BBA-NOS in dry dioxane was slowly added to the fibronectin or laminin solution in eguamolar amounts to the concentration of protein epsilon amino groups (lysine residues) by syringe drive at 4° C. in the dark over 16 hours. Then the mixture was stirred 4 hours in the cold. The fibronectin or laminin solution was centrifuged to remove insoluble material then applied to a Sephadex G-75 column to remove uncoupled photo reagent. The factions were monitored at 260 nm and 462 nm to assess the photogroup/protein ratios.

B. Covalent Binding of EGF, Collagen, and HSA to Chemical Linking Moieties.

Human placenta Type IV collagen (Sigma Pharmaceutical), endothelial growth factor (Sigma Pharmaceutical), and human serum albumin (Sigma Pharmaceutical) were separately dissolved at 2 mg/ml concentrations in 0.1 M borate, pH 9.0. solution of ANP-EAC-NOS in DMF, ANP-AUD-NOS in DMF or BBA-NOS in dioxane was slowly added to the solution containing the biocompatible agent in 5X molar amounts to the concentration of epsilon amino groups (lysine) residues by syringe drive at 4° C. in the dark over 16 hours. Then the solution was dialyzed against 4 1000ml changes of phosphate buffered saline (PBS) and centrifuged to remove insoluble material. The product was analyzed at 260 nm, 280 nm and 462 nm to assess the photogroup/protein ratios.

4. Covalently Binding the Biocompatible Agents to Plastic Surfaces.

Various sheets, tubes and flat pieces of polyethylene, polyvinyl chloride, polypropylene, polyurethane, Dacron ®️ (velour), Silastic ®️ (medical grade), and polytetrafluroethylene above were used. A 0.05 ml aliquot of solutions containing 0 to 500 ug/ml of photolabeled biocompatible agent was added to each 0.5 $cm^2$ section of plastic surface. The solution was allowed to adsorb onto each piece for 3 hours at room temperature in the dark. The excess liquid was removed and the biocompatible agents were covalently linked to the surfaces by photolysis for 12 hours at the appropriate wavelength (Tungsten "spotlite" for ANP and long wavelength UV for BBA). After photolysis, the specimens were washed with a 4 second stream of PBS to remove non covalently linked molecules of photolabeled biocompatible agent. The pieces were then placed in tissue culture to assess the endothelial cell reaction to the cell factors as follows.

5. In Vitro Tests Performed with Modified Surfaces.

A. Radio labeled biocompatible agents. Radiolabeled [$^3$H]biocompatible agents were photolabeled as described above and photocoupled to plastic surfaces. The plastics surfaces were extensively washed with PBS, then dissolved in organic solvent, and counted by liquid scintillation spectrometry. Some representative results are given in the Table 2.

TABLE 2

| Photolabeled Biocompatible Agent | Solid Surface | Sample results of amounts of growth factors photocoupled to various materials | | |
|---|---|---|---|---|
| | | Ng Growth Factor Applied/$cm^2$ | Ng Growth Factor Photocoupled/$cm^2$ | % Coupling Efficiency |
| ANP-EAC-FN | PVC | 843.04 | 677.6 | 80.4% |
| | Polyurethane | 843.04 | 823.04 | 97.6% |
| BBA-FN | PVC | 3564.0 | 1091.2 | 30.62% |
| | Polyurethane | 3564.0 | 2622.4 | 73.58% |
| ANP-EAC-COL | PVC | 2675.2 | 374 | 14.0% |
| | Polyurethane | 2675.2 | 2173.6 | 81.26% |
| BBA-COL | PVC | 1105.2 | 197.56 | 17.9% |
| | Polyurethane | 1105.2 | 920.3 | 83.3% |

As these results show the photolabeled biocompatible agents covalently coupled to these surfaces.

B. Attachment of Bovine Endothelial Cells to Modified Plastic Surfaces.

Bovine endothelial cells were collected from fetal animals 8-24" in length. Cornea, aorta and umbilical endothelial cells were harvested aseptically. Cells were grown in a 5% $CO_2$ incubator at 37° C. in a known high glucose cell growth medium such as Dulbecco s modified Eagle's medium (described in R. Dulbecco and G. Freeman, *Virology*, Vol. 8:396 (1959) and J. D. Smith, G. Freeman, M. Vogt and R. Dulbecco, *Virology*, Vol. 12:185-196 (1960)) with 25mmole HEPES buffer, 10% bovine calf serum, and 2.5 micrograms amphotericin B/ml (the "growth media"). Once the plates, tubes or sheets were prepared; cell cultures were prepared from primary cell lines. The cells were detached from the cell lines with a 0.25% solution of trypsin and resuspended in the growth media. Cells were then counted using a trypan blue (0.4%) solution and a hemocytometer. Various concentrations of cells were layered on the prepared materials. Cell attachment was monitored for various time periods from 5 minutes to 14 days. Attachments were determined by at least two methods. In one, sample materials were removed from culture media and washed 2 times with sterile saline. Cell stains were then applied and total cells on the surface were counted. A second method was to trypsinize the cells off the surface with a trypsin solution and count using the trypan blue method.

Represenive results of the attachment and outgrowth of endothelial cells on precoated polyvinyl chloride plastic pieces are reported in Table 3. The number of viable cells attached to each piece were determined by trypan blue staining procedures.

cells were trypsinized and counted with the trypan blue method. Cells were allowed to adhere to the prepared plastic for three hours to seven days. Cells were rinsed off and the total number of any results attached cells were compared to the number of non attached cells. Representative results appear in Table 3 above.

D.

Outgrowth Measurement using Endothelial Cells. The following techniques were used to monitor the outgrowth of cells from a point of origin as the cells grow to cover the surfaces of the plastics listed above modified as follows. Solutions of biocompatible agents containing from 0 to 500 micrograms of cell factors were coated onto surfaces from 1 to 6 cm long to establish a gradient. Cells were not detached from the tissue with trypsin or any proteinase. The tissue was placed on a point of origin at the low end of the gradient and marked. The tissue was allowed to sit for 15 minutes at room temperature. Growth media was added to give a moist coating over the plastic. All protocols were carried cut using aseptic conditions. Plates were then incubated at 37° C. in a 5% $CO_2$ incubator. Outgrowth was measured daily for up to two weeks or until the length of plastic was completely covered. Outgrowth on the treated surfaces was compared to nontreated control surfaces as reported in Table 3 above. All materials were rinsed and stained for permanent scanning electron microscopy.

These results demonstrated that the covalent attachment of the growth factors fibronectin (FN) and collagen (COL) to the plastic surface improved the biocompatibility of the plastic with bovine endothelial cells. The cells preferentially attached to the modified surfaces versus control surfaces as is indicated by the dis-

TABLE 3

| Biocompatible agent and chemical-linking moiety | Cell attachment determinations and outgrowth of endothelial cells on the treated polyvinyl chloride surface. | | | |
|---|---|---|---|---|
| | Ng growth factor/$cm^2$ | 3-day cell counts* | 7-day cell counts | 7-day outgrowth* |
| ANP-EAC-FN | 677.6 | 2610(2+ —3+) | 3539(2+ —3+) | 1.5-1.75 mm(2+) |
| BBA-FN | 1091.2 | 868(1+ —2+) | 14500(2+) | 3.75-4.25 mm(2+ —3+) |
| ANP-EAC-COL | 374.0 | 14500(3+ —4+) | 15833(2+ —3+) | 1.0-3.0 mm(3+) |
| BBA-COL | 197.6 | 5749(2+) | 21500(3+) | 2.5-4.0 mm(3+) |
| Control PVC | | 0 | 7(2+) | 1.5-2.0 mm(3+) |

C. Attachment of Human Umbilical Endothelial Cells.

Primary human endothelial cells were harvested from fresh (less than 4 days old) human umbilical cords. Cords were rinsed with 20 mls cord buffer (0.144M NaCl, 0.004M KCl and 0.001M $PO_4$) twice to remove blood and clots. Collagenase was pushed into the cord and left for 20 minutes at room temperature. Using 10 ml of warm cord buffer, the collengenase and detached cells were flushed into tubes. The suspension in the tubes were combined and centrifuged at 1500 rpm for 5-10 minutes. The supernatant was poured off and the cells resuspended in 10 ml of cord buffer. Following the second centrifugation, the cells were resuspended in cord buffer and plated into tissue culture disks. All cells were incubated in 37° C. incubator with 5% $CO_2$. Cells were radiolabeled using $^{51}Cr$ in cord media without calf serum.

Labeled cells were then used for cell attachment studies. Plates, sheets, and tubes of the plastics described above were prepared as recorded above. The tance they grew out over the plastic surface.

6. In Vivo Studies.

Two conditioned dogs were obtained for this study. Pieces of GORE-TEX (reinforced expanded polytetrafluroethylene, a trademarked product of W. L. Gore and Associates, Inc.) were precoated with FN, ANP-EAC-FN (adsorbed and photocoupled), ANP-EAC-FN (adsorbed only) and a PBS control. The testing was a blind study. The grafts were labeled by lettering; however, the surgical team did not know which grafts had modified surfaces and which were controls. Each dog received two 6 mm×5 cm pieces of GORE-TEX implanted in the left and right iliac artery. The grafts were left in the dogs for one month (30 days). The dogs were given the anti-inflammatory drugs Persontine and Aspirin to mimic human implant procedures.

Both control grafts (PBS and FN) were patent and had sufficient caliber. The anastomatic lines were intact and the inner surfaces were smooth. Endothelialization was incomplete with the control grafts. There appeared to be no evidence of significant thrombosis. Both grafts to which ANP-EAC-FN was bound (photocoupled and adsorbed only) were free of thrombosis formation. Endothelialization was complete giving the inner surfaces of the grafts a smooth, shiny appearance.

EXAMPLE 2

Modification of the Surfaces of Contact Lenses and Introcular Lens Implants

The experiments described in this example involved preparations of hydrophilic polymers (a biocompatible agent) bound to a chemical linking moiety, photocoupling the moieties to contact lens surfaces, and measuring the in vitro protein deposition from artificial tear solutions onto these lenses in comparison to non treated lenses. Experiments to study the compatibility of the biocompatible agents in vitro with corneal pieces and in vivo in rabbit eyes were conducted to assure that there were not toxic or irritant reactions to the resulting lenses.

1. Binding Biocompatible Agents to the Chemical Linking Moiety.

A. Preparation of Photolabeled Polyethylene Glycols.

Polyethylene glycols of molecular weights 1000 (PEG-1000) and 4000 (PEG-4000) were labeled with fluoronitroazidobenzene (FNAB) by modification of the phase transfer method of "Kimura, and S. Regen, Journal of Organic Chemistry 48; 195 (1983) the teachings of which are incorporated by reference herein. Briefly, the phase transfer synthesis of 4-azido 2-nitrophenyl polyethylene glycol (ANP-PEG) involved the mixture of 60% aqueous potassium hydroxide ("KOH")/toluene with FNAB and PEG, followed by extraction and thin layer chromatographic (TLC) purification as described below.

ANP-PEG-1000.

ANP-PEG-1000 was prepared by adding 0.05 mmole PEG-1000 to 5 mls 60% KOH and 0.5 mmole FNAB to 10 ml toluene. This reaction mixture was rapidly stirred at room temperature for 16 hours. The product was isolated from the organic layer. TLC in 85/15/1/1 chloroform/methanol/$H_2O$ acetic acid or ammonium hydroxide separated mono and di-substituted derivatives of ANP-PEG-1000 from unlabeled PEG. The band corresponding to ANP-PEG-1000 (lower $R_f$ value) was extracted from silica gel with TLC solvent and azeotrophed to remove residual acid or base. The final product was soluble in water and resulted in the conversion of 30–40% of the PEG starting material to ANP-PEG-OH product.

ANP-PEG-4000. The ANP-PEG-4000 was prepared by the same procedure as that described above except that the reaction mixture was rapidly stirred at 50° C to ensure all reagents remained in solution during the course of the reaction. The yield of ANP-PEG-4000-OH was 10%.

B. Preparation of Photolabeled Jeffamines.

Polyoxypropylenepolyamines and polyoxyethylenepolyamines (referred to as "Jeffamines", a trademark of Jefferson Chemical Co., Inc.) were photolabeled by coupling the N-oxysuccinimide ("NOS") esters of ANP-EACA, BBA and nBBA to the polymers. These NOS-derivatives were added in 0.5X amounts to 1X Jeffamine in very dry (high purity) solvents (ANP-EAC-NOS in dry tetrahydrofuran, BBA-NOS in dry dioxane or dimethylformamide and nitro BBA-NOS in dry dioxane or dimethylformamide). After 16 hours of reaction at room temperature in the dark, the products were isolated by TLC in 85/15/1/1/ chloroform/methanol/$H_2O$/acetic acid. Monosubstituted Jeffamine derivatives were extracted with the TLC solvent and azeotrophed with water to remove the residual acetic acid. The water soluble products ANP-EAC-Jeffamine, BBA-Jeffamine, and nBBA-Jeffamine were isolated in 15%, 10% and 12% yields, respectively.

C. Preparation of ANP-Hyaluronic Acid.

The terminal sugar of human placental hyaluronic acid ($MW_{app}$ 100–130,000) was activated by the periodate procedure described in E. Junowicz and S. E. Charm, "The Derivatization of Oxidized Polysaccarides for Protein Immobilization and Affinity Chromatography," *Biochimica et Biophysica Acta*, Vol. 428: 157 165 (1976) and incorporated herein by reference. This procedure entailed adding sodium or potassium periodate to a solution of hyaluranic acid thus activating the terminal sugar The hyaluronic acid was added to a 10-fold excess of Jeffamine and allowed to react 4 hours at room temperature. The linkages were stabilized by reduction with sodium cyanoborohydride, followed by exhaustive dialysis to remove most of the excess Jeffamine. A 10 fold molar excess of ANP-EAC-NOS in DMF was added to the Jeffamine hyaluronate in 0.1M carbonate, pH 9.0, by syringe drive. This addition required 16 hours and was conducted at room temperature in the dark. The excess ANP-EAC-NOS and ANP-EAC-Jeffamine was removed by gel filtration chromatography. The integrity of the azide group, which is required for photocoupling of the moiety to the contact lens polymer backbone was analyzed by infrared spectroscopy to detect the ANP group, a polyethylene glycol assay to detect the Jeffamine spacer, and a modified carbazole assay described in T. Bitter and H. Muir, *Analytical Biochemistry* Vol 4: 330–334 (1962) and incorporated herein by reference to determine the uronic acid content of the derivative.

The polyethylene glycol assay was developed using the Dragendorff reagent (tetraiodobismuthic acid-barium chloride). A 5-ml portion of stock reagent 425 mg bismuth nitrate, 10-gm potassium iodide in acetic acid and water was added to 10-ml 10% barium chloride in water and a background reading at 516+nm was noted. Then 0.1-ml of the sample was added and the contents mixed by inversion of the cuvette. A reading was taken at 516-nm after 1 minute of incubation. The values were compared to a standard curve.

The carbazole assay was performed as follows. A 3.0 ml portion of sulfuric acid reagent (0.025M sodium tetraborate-10 $H_2O$ in sulfuric acid) was cooled to -70° C. A 0.5 ml portion of sample was layered onto the acid and the mixture wa stirred (30 min.) until it reached room temperature. The tubes were heated at 100° C. (10 min.), a 0.1 ml aliguot of carbazole reagent (0.125% carbazole in absolute ethanol) was added, the tube contents were mixed (5 min.), heated at 100° C. (15 min.), then cooled to room temperature in an ice bath. The samples were analyzed spectrophotometrically at 530 nm against a sulfuric acid reagent blank. The results were compared to a standard curve constructed with 4–40 ug/ml glucuronolactone standards. The assay was sensitive to detecting 20 pmole of hyaluronic acid.

The fractions containing one ANP, one Jeffamine and one hyaluronate molecule were pooled and used as a biocompatible agent.

D. Preparation of Photolabeled Hyaluronic Acid, Methyl Cellulose and Chondroitin Sulfate.

ANP-EAC-Jeffamine, BBA-Jeffamine and nitro BBA-Jeffamine were linked to the carboxyl groups of uronic acid residues of hyaluronic acid and chondroitin sulfate by a carbodiimide procedure as follows. A 5 molar excess of photolabeled Jeffamine and 1-ethyl-3-(3-dimethylaminopropyl) carbodiimide with HCl was mixed with the polysaccharide polymer in water adjusted to pH 4.5 with 0.1N HCl. The mixture was allowed to react at room temperature in the dark for 24 hours. The product was purified by gel filtration chromatography then analyzed for photogroup and carbohydrate content as described above.

E. Preparation of Photolabeled Collagen.

Human placenta Type IV collagen (available from Sigma Pharmacueticals) was dissolved at a 1 mg/ml concentration in 0.1M borate, pH 9.0. ANP-EAC-NOS in DMF, BBA-sulfa-NOS in dioxane or nitro BBA-NOS in dixoane was slowly added to the collagen solution in a 50× molar excess by syringe drive at 4° C. in the dark over 16 hours. After the addition was complete, the mixture was stirred 4 hours in the cold. The collagen product was dialyzed against 4 changes of PBS then centrifuged to remove insoluble material. The supernatant was measured spectrophotometrically at 260 nm, 280 nm and 462 nm to assess the photogroup/protein ratio.

F. Preparation of Photolabeled Proteinases.

ANP-EAC-NOS, BBA-NOS and nBBA-NOS photogroup dissolved in organic solvent at 25 mg/ml concentrations, were added in 50 molar excess to papain (papaya, MW 23,426) by syringe drive at 4° C. in the dark over 16 hours. After addition of the photogroup was completed, the mixture was stirred an additional 4 hours, then dialyzed in PDS to remove uncoupled photogroups. After dialysis, the product was centrifuged to remove insoluble material. The supernatant was measured spectrophotometrically at 260 nm, 280 nm, and 462 nm to estimate the photogroup/protein ratio.

2. Photocoupling Biocompatible Agents to Lens Surfaces.

The photolabeled biocompatibles agents obtained above were added to the contact lens materials described in Table 4 at a concentration of 250–1000 pmole agent/contact lens. The solution was allowed to adsorb onto the contact lenses at room temperature in the dark for 3 hours. The photolabeled agents were then covalently linked to the plastic by photolysis for 12 hours at the appropriate wave length (450 nm for ANP and 320 nm for BBA and nBBA derivatives). After photolysis, the contact lenses were washed with 5×5 ml of normal saline (0.85% NaCl) to remove non covalently linked groups.

Radiolabeled groups may be coupled to the lens materials, and the lens pieces treated with tetrahydrofuran followed by DMSO to release the radiolabel from the solid surface. Scintillation fluor is then added and the amount of biocompatible agent/$cm^2$ determined by liquid scintillation spectroscopy. Representative results are shown in Table 4.

TABLE 4

| Biocompatible Agent | Load Densities of Biocompatible Agents on Various Contact Lens Materials | | | |
|---|---|---|---|---|
| | Contact Lens Material | *pmole/$cm^2$ | ng/$cm^2$ | Coupling Efficiency |
| ANP-1000 | Polyvinyl chloride | 19.96 | 19.96 | 22.86% |
| | Sofspin (polymacon) | 33.45 | 33.45 | 12.95% |
| | Permaflex | 33.97 | 33.97 | 12.90% |
| | Vistamarc | 34.26 | 34.26 | 13.20% |
| | Lidofilcon | 63.12 | 63.12 | 24.30% |
| | Silicone | 33.97 | 33.97 | 4.80% |
| | **Polymacon Button | 2408.60 | 2408.60 | 38.23% |
| ANP-4000 | Sofspin (polymacon) | 27.06 | 108.24 | 10.50% |
| | Permaflex | 42.86 | 171.44 | 16.50% |
| | Silicone | 170.60 | 682.40 | 22.70% |
| | **Polymacon Buttons | 1574.00 | 6296.00 | 25.00% |
| nitro BBA-2000 | Polyvinyl Chloride | 23.20 | 46.40 | 26.60% |
| | Sofspin | 13.14 | 26.28 | 5.10% |
| | Permaflex | 8.21 | 16.42 | 3.20% |
| | Silicone | 95.61 | 191.22 | 13.50% |
| | **Polymacon Buttons | 3738.00 | 7476.00 | 56.45% |
| BBA-2000 | Silicone | 113.20 | 226.40 | 15.60% |
| | **Polymacon Buttons | 4035.10 | 8070.20 | 64.30% |
| ANP-Hyaluronic acid | Silicone | 25.00 | 25.00 | 7.00% |
| | **Polymacon Buttons | 130.95 | 130.95 | 7.90% |

*Values were averaged from replicates of 10
**Polymacon loads are based on total volume, $cm^3$, rather than surface area.
Sofspin contacts are made of polymacon (polymethacrylate) with about 38.6% water and are a trademarked product of Bausch & Lomb, Inc.
Permaflex contacts are made of polymethacrylate with about 74% water and are a trademarked product of Coopervision, Inc.
Vistamarc contacts are made of polymethacrylate with about 58% water and are a trademarked product of Johnson & Johnson.
Lidofilcon contacts are made of polymethacrylate with about 70% water and are a product of Bausch & Lomb, Inc.

The values in Table 4 are expressed a pmole biocompatible agent per square centimeter surface area or ng/$cm^2$.

The coupling efficiencies were based upon addition of 260 pmole/$cm^2$ biocompatible agent/contact lens materials, 710 pmole/$cm^2$ biocompatible agent/ silicone, and 660 pmole/$cm^3$ biocompatible agent/$cm^3$ polymacon button. ANP-hyaluronate was added at 357 pmole/cm2 to silione and at 1655 pmole/$cm^3$ to polymacon button material. The ANP-derivatives coupled at higher load densities than the nBBA-Jeff on the hydrogel contact lens materials. These results were reversed for the silicone compound.

3. In Vitro Protein Adsorption Studies. Artificial human tears were prepared according to the formula found in B. P. Gloor, "The Lacrimal Apparatus" in *Adler's Physiology of the Eye: Clinical Applications* (R. A. Moses, ed.), C. V. Mosby Co., St. Louis, Mo. (1981) the teachings of which are incorporated herein. As indicated in that reference the major proteins present in human tears are serum albumin (HSA), gamma-globulin (HGG), and lysozyme (LYZ). The major sterols present in human tears are cholesterol and cholesterol esters.

A. $^3$H Proteins.

The protein components were tritiated by reductive methylation with formaldehyde and tritiated sodium borohydride as described in N. Jentoft and D. C. Dearborn, *Journal of Biochemistry*, Vol. 254: 4359–4365 (1979) and incorporated herein by reference. Briefly, the biocompatible agent in 1 mg/ml concentration in 0.1M HEPES, pH 7.4 was methylated by formaldehyde reacting with tritiated sodium borohydride and rocking at 22° C. for about 2 hours. The product was dialyzed against PBS in 0.01M phosphate, 0.15M sodium chloride, pH 7.4, and affinity purified on gelatin sepharose. Bound agent was eluted with 1M sodium bromide 0.02M sodium acetate, pH 5.0 then dialyzed against PBS, pH 7.4.

B. Preparation of Artificial Tears.

The radiolabeled proteins described above were used in preparation of artificial tears. One of the radiolabeled proteins or the tritiated cholesterol was included in each tear mixture. The other components were not radiolabeled. The contact lens materials were incubated in the artificial tear solution for one week at 37° C. with gentle agitation. At the end of this time the lens materials were washed with 5×10 ml of 0.85% NaCl. The amount of protein adsorbed to the lens materials was then determined by liquid scintillation counting.

In vitro protein deposition results are given in Table 5. Reduction in total protein deposition reached 85% in ANP-1000-OH modified Sofspin lenses. Individual biocompatible agents increased or stayed at the same levels as some of the control contact lens materials, but the overall protein amounts were reduced for all lens materials except ANP-1000-OH coated Polymacon buttons, ANP-4000-OH coated polymacon buttons and ANP hyaluronate coated polymacon buttons. These poor results were all obtained with virgin polymacon materials which appears to react differently than polymacon contact lenses, such as Sofspin lenses. Overall, these in vitro protein deposition studies demonstrated significant to dramatic decreases in protein deposition from artificial tears on various contact lens materials during a one week period.

TABLE 5

In Vitro Proteins Adsorption from Artificial Tears: $^3$H Proteins*

| Biocompatible Agent | Contact Material | ugHSA/ cm$^2$ | % of control | ugHgg/ cm$^2$ | % of control | ugLys/ cm$^2$ | % of control | ug Total Protein | % of control | % Reduction Total Protein |
|---|---|---|---|---|---|---|---|---|---|---|
| Controls | Polyvinyl Chloride | .525 | 100.pp | .524 | .441 | | 1.49 | | | |
| | Sofspin (Polymacon) | 1.256 | | 1.33 | | .576 | | 3.162 | | |
| | Permaflex | .978 | | 1.953 | 1.866 | | 4.797 | | | |
| | Vistamarc | .553 | | .343 | 47.86 | | 48.76 | | | |
| | Lidofilcon | 2.154 | | 1.009 | 1.423 | | 4.586 | | | |
| | Silicone | 1.121 | | .272 | .264 | | 1.657 | | | |
| | **Polymacon Buttons | 32.23 | | 6.983 | 2.46 | | 41.673 | | | |
| ANP-1000-OH | Polyvinyl Chloride | .298 | 56.8 | .696 | 133 | .0384 | 8.7 | 1.032 | 69.3 | 30.7 |
| | Sofspin | .241 | 19.2 | .191 | 14.4 | .04 | 6.9 | .472 | 14.93 | 85.07 |
| | Permaflex | .582 | 59.5 | 1.351 | 69.2 | 1.693 | 90.73 | 3.626 | 75.6 | 24.4 |
| | Vistamarc | .187 | 33.8 | .378 | 110.2 | 39.19 | 81.88 | 39.76 | 81.5 | 18.5 |
| | Lidofilcon | .640 | 29.7 | .440 | 43.6 | 1.73 | 121.5 | 2.81 | 61.3 | 38.8 |
| | Silicone | .103 | 9.2 | 1.016 | 373.5 | .214 | 81.1 | 1.333 | 80.4 | 19.6 |
| | **Polymacon Buttons | 36.00 | 111.0 | 5.44 | 77.9 | 2.47 | 100.0 | 43.91 | 105.4 | (−5.4) |
| ANP-4000 | Polyvinyl Chloride | .430 | 81.9 | .356 | 67.9 | .148 | 33.6 | .934 | 62.7 | 37.3 |
| | Sofspin | 1.16 | 92.4 | .608 | 45.7 | .297 | 51.6 | 2.065 | 65.3 | 34.7 |
| | Vistamarc | .187 | 33.8 | .686 | 200.0 | 43.24 | 90.3 | 44.11 | 90.5 | 9.5 |
| | Silicone | 1.082 | 96.5 | .242 | 88.9 | .210 | 79.5 | 1.534 | 92.6 | 7.4 |
| | **Polymacon Buttons | 37.62 | 116.7 | 4.172 | 59.7 | 1.863 | 75.7 | 43.655 | 104.7 | (4.7) |
| nBBA-Jeff | Polyvinyl Chloride | .632 | 120.3 | .576 | 109.9 | .072 | 16.33 | 1.28 | 85.9 | 14.1 |
| | Sofspin | .665 | 52.9 | .859 | 64.5 | .531 | .922 | 2.055 | 64.9 | 35.1 |
| | Silicone | .978 | 87.2 | .061 | 22.4 | .068 | 25.8 | 1.107 | 66.8 | 33.2 |
| | **Polymacon Buttons | 26.35 | 81.76 | .01 | .14 | .01 | .41 | 26.37 | 63.28 | 36.72 |
| BBA-Jeff | Polyvinyl Chloride | .326 | 62.1 | .454 | 86.6 | .290 | 66.7 | 1.07 | 71.8 | 28.2 |
| | Silicone | .921 | 82.15 | .089 | 32.7 | .149 | 56.4 | 1.159 | 69.9 | 30.1 |
| | **Polymacon Buttons | 30.61 | 94.9 | 3.695 | 52.9 | .01 | .40 | 34.32 | 82.34 | 17.66 |
| ANP-Jeff | Polyvinyl Chloride | .486 | 92.6 | .456 | 87.0 | .192 | 43.5 | 1.134 | 76.1 | 23.9 |
| | Silicone | .904 | 80.6 | .231 | 83.7 | .257 | 97.6 | 1.392 | 84.01 | 15.99 |
| | **Polymacon Buttons | 35.48 | 110.1 | 5.62 | 80.5 | 1.94 | 78.86 | 43.04 | 103.3 | (3.3) |

TABLE 5-continued

| | | In Vitro Proteins Adsorption from Artificial Tears: $^3$H Proteins* | | | | | | | |
|---|---|---|---|---|---|---|---|---|---|
| Biocompat- ible Agent | Contact Material | ugHSA/ cm$^2$ | % of control | ugHgg/ cm$^2$ | % of control | ugLys/ cm$^2$ | % of control | ug Total Protein | % of control | % Reduction Total Protein |
| | Buttons | | | | | | | | | |

*The values are calculated from 10 replicates
**Polymacon buttons are based on volume rather than surface area cm$^3$
***Values in parenthesis indicate an increase in protein adsorption The results of the in vitro cholesterol deposition studies are given in Table 6. The amount of cholesterol deposition after 7 days of incubation in artificial tears was reduced by as much as 83% on polyvinyl chloride. All contact lens types exhibited reduction of cholesterol deposition except the polymacon button pieces. Again, these materials react differently than the contact lenses made of the same polymer.

TABLE 6

Cholesterol Adsorption from Artificial Tears: $^3$H Cholesterol

| Biocompatible Agent | Contact Material | *ug Cholesterol/ cm$^2$ | % of Control | % Reduction |
|---|---|---|---|---|
| Controls | Polyvinyl Chloride | .096 | 100 | 72.9 |
| | Sofspin | .091 | 100 | |
| | Permaflex | .196 | 100 | |
| | Vistamarc | .032 | 100 | |
| | Lidofilcon | .053 | 100 | |
| | Silicone | .103 | 100 | |
| | Polymacon Button | .215 | 100 | |
| ANP-1000 | Polyvinyl Chloride | .026 | 27.1 | 72.9 |
| | Sofspin | .075 | 82.4 | 17.6 |
| | Permaflex | .134 | 68.4 | 31.6 |
| | Vistamarc | .028 | 87.5 | 12.5 |
| | Lidofilcon | .046 | 86.8 | 13.21 |
| | Silicone | .086 | 83.5 | 16.5 |
| | Polymacon Button | .245 | 113.9 | **(13.9) |
| ANP-4000 | Polyvinyl Chloride | .0166 | 17.3 | 82.7 |
| | Sofspin | .101 | 110.9 | (10.9) |
| | Permaflex | .134 | 68.4 | 31.6 |
| | Vistamarc | .023 | 71.9 | 28.1 |
| | Silicone | .104 | 100.9 | (0.9) |
| | Polymacon Buttom | .248 | 115.3 | (15.3) |
| nBBA-Jeff | Polyvinyl Chloride | .038 | 39.6 | 60.4 |
| | Sofspin | .138 | 151.6 | (51.6) |
| | Permaflex | .164 | 83.7 | 16.33 |
| | Silicone | .072 | 69.9 | 30.1 |
| | Polymacon Button | .148 | 68.8 | 31.2 |
| BBA-Jeff | Polyvinyl Chloride | .0214 | 22.3 | 77.7 |
| | Silicone | .107 | 103.8 | (3.8) |
| | Polymacon Button | .230 | 106.9 | (6.9) |
| ANP-Jeff | Polyvinyl Chloride | .028 | 29.2 | 70.2 |
| ANP- Hyaluronate | Silicone | .224 | 217.5 | (117.5) |
| | Polymacon Button | .238 | 110.6 | (10.6) |

*Values were the averages of ten replicates.
**Values in parentheses indicate increase in cholesterol adsorption.

C. Amino Acid Analysis.

Control and surface modified lenses were incubated in the artificial tear solution for one week at 37° C. with gentle agitation. The lenses were washed with 5 10ml washes of 0.85% NaCl, then hydrolyzed with 6N HCl and the hydrolysates subjected to standard amino acid analyses on an amino acid analyzer. Total amino acid content of control and surface modified lenses were compared to each other. Reduction in total amino acid content indicated a reduction in protein absorption.

The total amino acid analyses of the acid hydrolyzed contact lenses are given in Table 8. These results are expressed as total amino acids in nmole/ml. These results again indicated that the ANP-1000-OH, ANP-4000-OH and nBBA Jeff modifications of Sofspin polymacon lenses reduced the deposition of proteins on the lenses after 7 days of incubation in artificial human tears.

TABLE 7

| | Total Amino Acid Analyses from Artificial Tear Deposits on Contact Lenses | | |
|---|---|---|---|
| Contact Material | Biocompatible Agent | Total Amino Acids nmol/lens no NH$^3$ | % Reduction |
| Sofspin | ANP-1000 | 62.75 | 59.7 |
| | ANP-4000 | 136.272 | 12.4 |
| | nBBA-Jeff | 105.381 | 32.3 |
| | Control | 155.616 | — |
| Permalens | ANP-1000 | 168.714 | 32.5 |
| | ANP-4000 | 210.207 | 15.9 |
| | nBBA-Jeff | 181.302 | 27.5 |
| | Control | 249.939 | — |

4. In Vitro Toxicity Testing.

The biocompatible lens materials described above were tested for irritant or toxicity responses. Control and biocompatible lenses were prepared under sterile conditions with final washing procedures conducted in a laminar flow hood. The lenses were placed in a solution of a known high glucose cell medium such as Dulbecco's Modified Essential Medium, with 10% fetal calf serum, and 5% glutamine (to which antibiotic and antifungal agents had been added). Pieces of viable 3-5 month fetal bovine corneas were placed on top of the lenses. The epithelial surface of the cornea was placed in contact with the lens surface in some studies and the endothelial cell surface was placed directly on the lens surface in other studies. The systems were placed in culture at 7-10% $CO_2$ and 37° C. for 1-2 week periods. At various intervals after initiation of culture the viabilities of the epithelial and/or endothelial cells were assessed by staining procedures. 5. In Vitro Assay for Stability of Covalent Bond.

The stability of the covalent attachment was assessed by subjecting the surface-modified polymacon (polymethacrylate) to enzymatic cleaner (papain), thermal disinfection and chemical disinfection (buffered acqueous solution containing sodium chloride, sodiumborate and boric acid.) These results are given in Table 8.

TABLE 8
Stability of Covalent Linkage to Cleaning Disinfection Procedures

| Biocompatible Agent | Treatment | pmole/cm3 | % Remaining |
|---|---|---|---|
| ANP-1000 | No treatment | 831 | 100 |
| | Enzymatic cleaner | 862 | 100 |
| | Boiling | 761 | 91.6 |
| | Chemical cleaner | 721 | 86.8 |
| ANP-4000 | No treatment | 1574 | 100 |
| | Enzymatic cleaner | 2012 | 100 |
| | Boiling | 2092 | 100 |
| | Chemical cleaner | 1564 | 99.4 |
| nBBA-2000 | No treatment | 1732 | 100 |
| | Enzymatic cleaner | 1785 | 100 |
| | Boiling | 1795 | 100 |
| | Chemical cleaner | 1129 | 65.2 |
| BBA-2000 | No treatment | 1651 | 100 |
| | Enzymatic cleaner | 1996 | 100 |
| | Boiling | 1619 | 98.1 |
| | Chemical cleaner | 1409 | 85.3 |
| ANP-Hyaluronate | No treatment | 300 | 100 |
| | Enzymatic cleaner | 317 | 100 |
| | Boiling | 340 | 100 |
| | Chemical Cleaner | 307 | 100 |

*Values are the averages of 10 replicates

The covalent linkages remained 100% stable to enzymatic cleaning and thermal disinfection. There was some loss of biocompatible agent with the chemical disinfection procedures except for the ANP hyaluronate. 6. In Vivo Assessment of Biocompatibility.

Preliminary in vivo biocompatibility testing was conducted in rabbit model systems. A population of at least 24 animals was used in each study. Scleral lenses designed to fit rabbit eyes were used in these studies. The rabbits wore lenses according to the following schedule:

| 6 rabbits | No lens left eye, control lens right eye |
| 6 rabbits | Control lens left eye; physically treated lens (same physical treatment as surface modified lenses but not coated with biocompatible agent) right eye |
| 12 rabbits | Control lens left eye; surface-modified lens right eye. |

The rabbits were anesthetized with Ketamine/Xylazine prior to placing the lenses in the rabbit eyes. A methyl cellulose/normal saline wetting solution was applied hourly to maintain adequate eye and lens lubrication. The contacts were worn 8 hours/day. After chosen periods of lens wear the rabbits were analyzed by slit lamp and fluorescein dye methods. The degree of eye irritation was graded by the McDonald Shadduck scale as described in T.0. McDonald and J. A. Shadduck, "Eye Irritation," in *Advances in Modern Toxicology*, Vol. 4, pp. 162-166 (1977) incorporated herein by reference. The McDonald-Shadduck procedure allows the investigator to grade conjuctival congestion, conjuctival swelling, conjunctival discharge, aqueous flare, iris involvement and corneal cloudiness and other characters on a scale of 0-4, with 0 being normal and +4 the most complete involvement.

The results of the in vivo rabbit studies are given in Table 9. The McDonald-Shadduck scores for the rabbits are represented in the table. Mann-Whitney U tests were performed on these results and indicated that there were no statistical differences between the surface-modified and control lenses ($p < 0.05$). Therefore, these tests indicate that in this 4-day study in rabbits, no detectable differences in conjunctival congestion, conjunctival swelling, conjuntival discharge, aqueous flare, iris involvement, corneal cloudiness, pannus vascularization, norepithelial damage of the surface modified lenses was detected as compared to control lenses. The irritation which was demonstrated in the control and the modified lenses appeared to be associated with the rabbits' development of tolerance to contact lenses.

TABLE 9

| Average McDonald-Shadduck Scores For In Vivo Rabbit Study | | | | |
|---|---|---|---|---|
| | Day 1 | Day 2 | Day 3 | Day 4 |
| Control Lens | 0.53 | 0.78 | 0.19 | 0.33 |
| Surface Modified Lens | 0.58 | 0.65 | 0.17 | 0.21 |

EXAMPLE 3

Coupling of Albumin, Heparin and Urokinase to Polyurethane Tubing

1. Preparation of Photolabeled Albumin.

Serum albumin (canine) was dissolved in 0.1M borate buffer at pH 9.0. A volume of 4 azido-2-nitrophenyl-6-aminocaproyl-N-oxysuccinimide (ANP-EAC-NOS) solution at 25 mg/ml in DMF to provide a 10 fold molar excess of ANP-EAC-NOS over albumin was added to the albumin with stirring at room temperature in the dark over about 12 hours using a syringe drive. The solution was then dialyzed in the dark against three one liter volumes of phosphate buffered saline (PBS). After dialysis, the solution was centrifuged to remove insoluble material. The absorance at 470 nm of a 1/100 dilution was measured spectrophotometrically to estimate the ANP/albumin ratio.

2. Photocoupling of Albumin to Polyurethane Tubing.

Polyurethane tubing was dipped into dioxane for thirty seconds after which it was immediately rinsed with deionized water. The etched tubing was immersed in a solution of photoreactive albumin for at least two hours at room temperature in the dark with mixing. The tubing was then air dried for at least ten minutes in the dark, then exposed to high intensity visible light for at least one hour. The immersion in photo reactive albumin, drying and photolyzing was repeated twice, the last time the dipping was left overnight. The tubing was then washed in 1.0 N NaCl for one hour at room temperature. The NaCl solution was changed at least once during the one hour.

3. Coupling of Heparin to Albumin on Polyurethane Tubing.

The albumin polyurethane tubing was immersed in 5.0 ml. of deionized water. 200 mg of 1-ethyl-3-(3-dimethylaminopropyl) carbodimide (EDC) was dissolved in the water, then the pH wa adjusted to 4.0 with 1N HCl. One ml of water containing 30 mg of heparin was added to the EDC solution. The pH was again adjusted to 4.0 with 1N HCl. The solution containing the immersed polyurethane tubing was mixed for two hours at room temperature after which another 200 mg of EDC was added. The reaction was then allowed to continue overnight at room temperature. The tubing was then rinsed in PBS to remove uncoupled heparin and reaction biproducts.

4. Coupling of Urokinase to Albumin on Polyurethane Tubing.

Polyurethane tubing having serum albumin immobilized thereon was immersed in 1.25% glutaraldehyde in 0.1M phosphate buffer, pH 7.0 for 15-18 hours at room temperature. The tubing was then washed in deionized water for 30 minutes, the water being changed at least once during that time. The polyurethane-albumin glutaraldehyde was then immersed in a solution of urokinase (8.3 units/ml, 2-3 mg/ml) in 0.1M borate of pH 9.0 and mixed overnight at 4° C. The tubing was then rinsed for four hours in PBS after which it was assayed for urokinase activity.

Two polymers were used as the solid surface, polyurethane and polyhema. The modified surfaces yielded 1-10 mg heparin/cm$^2$ an 0.6-1.3 mg urokinase/cm$^2$.

EXAMPLE 4

Coupling of a Film to a Solid Surface Formation of a Coating Film and its Covalent Attachment to a Surface.

Preparation of ANP-hyaluronic acid.

Photolabeled derivatives of hyaluronic acid (ANP EAC Jeffamine, BBA-Jeffamine and nitro-BBA-Jeffamine) were prepared as previously described.

Films are formed from the photoreactive coating material and placed on surfaces of contact lenses (by dipping and drying) in the dark. Covalent attachment to the biomaterial surface and strengthening of the film by intermolecular cross-linking may be accomplished through illumination.

In another example, an artificial hip joint is soaked in ANP-EAC-Jeffamine hyaluronic acid (.1:1 mg/ml) for three hours in the dark. The joint is then removed from solution and allowed to dry forming a thin film of coating material on the artificial joint. The film is then covalently attached to the joint by illumination at 400 to 450 nm for 8 hrs. at 4° C. The joint is then rinsed in physiological saline to remove uncoupled ANP-EAC-Jeffamine hyaluronate. The hyaluronic acid bound to the bone reduces friction and reduces wearing of the bone in the joint area.

100 mg of bovine serum albumin is dissolved in 2 ml of 0.1M borate buffer pH 9. 14 mg of ANP-AUD-NOS is dissolved in 50 ul of dimethylformamide (DMF). The ANP-AUD-NOS solution is added to the BSA solution slowly over 15 hrs at room temperature in the dark with good stirring. After an additional 3 to 4 hours of stirring the solution is dialyzed against 0.1M borate buffer at pH 9 in the dark over 24 hrs. with at least 4 changes of 2 liters each of buffer. The dialyzed ANP-BSA is pipetted onto paraffin films in 100 ul aliquots and dried in the dark. After the films have dried they are overlaid with 100 ug aliquots of 1.25% glutaraldehyde and borate buffer pH 9 and incubated for one hour at room temperature in the dark. The films are then washed by slowly dropping water onto them while still on the paraffin films and allowing the water to run off. After one hour of such washing, the films are redried and then carefully lifted off the paraffin film and transferred to a plastic surface (e.g., polyurethane). On the plastic surface the films are again wetted with water containing 20% dioxane, then redried in the dark. The films on the plastic surfaces are then exposed to high intensity visible light for four hours at 4° C. to bind the film to the surface with a fan blowing across the surface to prevent excessive heating of the surface.

While a preferred embodiment of the present invention has been described, it should be understood that various changes, adaptations and modifications may be made therein without departing from the spirit of the invention and the scope of the appended claims.

What is claimed is:

1. A method of providing a device with an effective biocompatible surface of a growth factor the method employing a solid surface of the device, molecules of the growth factor and a chemical linking moiety possessing a photochemically reactive group capable upon activation of covalently bonding to the solid surface, and possessing a different reactive group, capable of binding to the molecules of the growth factor, one of the groups being unresponsive to a stimulus to which the other group responds, the method comprising:

activating the different reactive group of the chemical linking moiety in the presence of the molecules of the growth factor to cause the different reactive group to covalently bind the chemical linking moiety to the molecules; and activating the photochemically reactive group of the chemical linking moiety in the presence of the solid surface of the device to cause the photochemically reactive group to covalently bind to the solid surface and to bind the growth factor molecules to the solid surface in a sufficient population density of the molecules to effectively shield the solid surface and to provide a biocompatible effective surface.

2. A method of providing a device with an effective biocompatible surface of collagen the method employing a solid surface of the device, molecules of collagen and a chemical linking moiety possessing a photochemically reactive group capable upon activation of covalently bonding to the solid surface, and possessing a different reactive group, capable of binding to the molecules of collagen, one of the groups being unresponsive to a stimulus to which the other group responds, the method comprising:

activating the different reactive group of the chemical linking moiety in the presence of the molecules of collagen to cause the different reactive group to covalently bind the chemical linking moiety to the molecules; and activating the photochemically reactive group of the chemical linking moiety in the presence of the solid surface of the device to cause the photochemically reactive group to covalently bind to the solid surface and to bind the collagen molecules to the solid surface in a sufficient population density of the molecules to effectively shield the solid surface and to provide a biocompatible effective surface.

3. A method of providing a device with an effective biocompatible surface of albumin the method employing a solid surface of the device, molecules of albumin and a chemical linking moiety possessing a photochemically reactive group capable upon activation of covalently bonding to the solid surface, and possessing a different reactive group, capable of binding to the molecules of albumin, one of the groups being unresponsive to a stimulus to which the other group responds, the method comprising:
activating the different reactive group of the chemical linking moiety in the presence of the molecules of albumin to cause the different reactive group to covalently bind the chemical linking moiety to the molecules; and
activating the photochemically reactive group of the chemical linking moiety in the presence of the solid surface of the device to cause the photochemically reactive group to covalently bind to the solid surface and to bind the albumin molecules to the solid surface in a sufficient population density of the molecules to effectively shield the solid surface and to provide a biocompatible effective surface.

4. A method of providing a device with an effective biocompatible surface of an antimicrobial agent the method employing a solid surface of the device, molecules of the antimicrobial agent and a chemical linking moiety possessing a photochemically reactive group capable upon activation of covalently bonding to the solid surface, and possessing a different reactive group, capable of binding to the molecules of the antimicrobial agent, one of the groups being unresponsive to a stimulus to which the other group responds, the method comprising:
activating the different reactive group of the chemical linking moiety in the presence of the molecules of the antimicrobial agent to cause the different reactive group to covalently bind the chemical linking moiety to the molecules; and
activating the photochemically reactive group of the chemical linking moiety in the presence of the solid surface of the device to cause the photochemically reactive group to covalently bind to the solid surface and to bind the antimicrobial agent molecules to the solid surface in a sufficient population density of the molecules to effectively shield the solid surface and to provide a biocompatible effective surface.

5. The method of claim 4 wherein the antimicrobial agent is lysosyme.

6. The method of claim 4 wherein the antimicrobial agent is penicillin.

7. A method of providing a device with an effective biocompatible surface of heparin the method employing a solid surface of the device, molecules of heparin and a chemical linking moiety possessing a photochemically reactive group capable upon activation of covalently bonding to the solid surface, and possessing a different reactive group, capable of binding to the molecules of heparin, one of the groups being unresponsive to a stimulus to which the other group responds the method comprising: activating the different reactive group of the chemical linking moiety in the presence of the molecules of heparin to cause the different reactive group to covalently bind the chemical linking moiety to the molecules; and
activating the photochemically reactive group of the chemical linking moiety in the presence of the solid surface of the device to cause the photochemically reactive group to covalently bind to the solid surface and to bind the heparin molecules to the solid surface in a sufficient population density of the molecules to effectively shield the solid surface and to provide a biocompatible effective surface.

8. A method of providing a device with an effective biocompatible surface of a synthetic hydrophilic polymer capable of existing in contact with biological fluid or tissue of a living organism with a net beneficial effect on the organism, the method employing a solid surface of the device, molecules of the synthetic hydrophilic polymer and a chemical linking moiety possessing a photochemically reactive group capable upon activation of covalently bonding to the solid surface, and possessing a different reactive group, capable of binding to the molecules of the synthetic hydrophilic polymer, one of the groups being unresponsive to a stimulus to which the other group responds, the method comprising:
activating the different reactive group of the chemical linking moiety in the presence of the molecules of the synthetic hydrophilic polymer to cause the different reactive group to covalently bind the chemical linking moiety to the molecules; and
activating the photochemically reactive group of the chemical linking moiety in the presence of the solid surface of the device to cause the photochemically reactive group to covalently bind to the solid surface and to bind the molecules of the synthetic hydrophilic polymer to the solid surface in a sufficient population density of molecules to effectively shield the solid surface and to provide a biocompatible effective surface.

9. A method of providing a contact lens with an effective biocompatible surface of a hydrophilic polymer selected from the group consisting of polyethylene glycol, hyaluornic acid, methyl cellulose, collagen and chitosan, the method employing a solid surface of the lens, molecules of the hydrophilic polymer and a chemical linking moiety possessing a photochemically reactive group capable upon activation of covalently bonding to the solid surface, and possessing a different reactive group, capable of binding to the molecules of the hydrophilic polymer, one of the groups being unresponsive to a stimulus to which the other group responds, the method comprising:
activating the different reactive group of the chemical linking moiety in the presence of the molecules of the hydrophilic polymer to cause the different reactive group to covalently bind the chemical linking moiety to the molecules; and
activating the photochemically reactive group of the chemical linking moiety in the presence of the solid surface of the device to cause the photochemically reactive group to covalently bind to the solid surface and to bind the molecules of the hydrophilic polymer to the solid surface in a sufficient population density of molecules to effectively shield the solid surface and to provide a biocompatible effective surface.

10. A method of providing a device with an effective biocompatible surface of polyethylene glycol capable of existing in contact with biological fluid or tissue of a living organism with a net beneficial effect on the organism, the method employing a solid surface of the device, molecules of the polyethylene glycol and a chemical linking moiety possessing a photochemically reactive group capable upon activation of covalently bonding to the solid surface, and possessing a different reactive group, capable of binding to the molecules of the polyethylene glycol, one of the groups being unresponsive to a stimulus to which the other group responds, the method comprising:

activating the different reactive group of the chemical linking moiety in the presence of the molecules of the polyethylene glycol to cause the different reactive group to covalently bind the chemical linking moiety to the molecules; and activating the photochemically reactive group of the chemical linking moiety in the presence of the solid surface of the device to cause the photochemically reactive group to covalently bind to the solid surface and to bind the molecules of the polyethylene glycol to the solid surface in a sufficient population density of molecules to effectively shield the solid surface and to provide a biocompatible effective surface.

11. A method of providing a device with an effective biocompatible surface of hyaluronic acid capable of existing in contact with biological fluid or tissue of a living organism with a net beneficial effect on the organism, the method employing a solid surface of the device, molecules of the hyaluronic acid and a chemical linking moiety possessing a photochemically reactive group capable upon activation of covalently bonding to the solid surface, and possessing a different reactive group, capable of binding to the molecules of the hyaluronic acid, one of the groups being unresponsive to a stimulus to which the other group responds, the method comprising:

activating the different reactive group of the chemical linking moiety in the presence of the molecules of the hyaluronic acid to cause the different reactive group to covalently bind the chemical linking moiety to the molecules; and activating the photochemically reactive group of the chemical linking moiety in the presence of the solid surface of the device to cause the photochemically reactive group to covalently bind to the solid surface and to bind the molecules of the hyaluronic acid to the solid surface in a sufficient population density of molecules to effectively shield the solid surface and to provide a biocompatible effective surface.

12. A method of providing a device with an effective biocompatible surface of chitosan capable of existing in contact with biological fluid or tissue of a living organism with a net beneficial effect on the organism, the method employing a solid surface of the device, molecules of the chitosan and a chemical linking moiety possessing a photochemically reactive group capable upon activation of covalently bonding to the solid surface, and possessing a different reactive group, capable of binding to the molecules of the chitosan, one of the groups being unresponsive to a stimulus to which the other group responds, the method comprising:

activating the different reactive group of the chemical linking moiety in the presence of the molecules of the chitosan to cause the different reactive group to covalently bind the chemical linking moiety to the molecules; and activating the photochemically reactive group of the chemical linking moiety in the presence of the solid surface of the device to cause the photochemically reactive group to covalently bind to the solid surface and to bind the molecules of the chitosan to the solid surface in a sufficient population density of molecules to effectively shield the solid surface and to provide a biocompatible effective surface.

13. A method of providing a device with an effective biocompatible surface of methyl cellulose capable of existing in contact with biological fluid or tissue of a living organism with a net beneficial effect on the organism, the method employing a solid surface of the device, molecules of the methyl cellulose and a chemical linking moiety possessing a photochemically reactive group capable upon activation of covalently bonding to the solid surface, and possessing a different reactive group, capable of binding to the molecules of the methyl cellulose, one of the groups being unresponsive to a stimulus to which the other group responds, the method comprising:

activating the different reactive group of the chemical linking moiety in the presence of the molecules of the methyl cellulose to cause the different reactive group to covalently bind the chemical linking moiety to the molecules; and activating the photochemically reactive group of the chemical linking moiety in the presence of the solid surface of the device to cause the photochemically reactive group to covalently bind to the solid surface and to bind the molecules of the methyl cellulose to the solid surface in a sufficient population density of molecules to effectively shield the solid surface and to provide a biocompatible effective surface.

14. A method of providing a device with an effective biocompatible surface of a cell attachment factor capable of existing in contact with biological fluid or tissue of a living organism with a net beneficial effect on the organism, the method employing a solid surface of the device, molecules of the cell attachment factor and a chemical linking moiety possessing a photochemically reactive group capable upon activation of covalently bonding to the solid surface, and possessing a different reactive group, capable of binding to the molecules of the cell attachment factor, one of the groups being unresponsive to a stimulus to which the other group responds, the method comprising:

activating the different reactive group of the chemical linking moiety in the presence of the molecules of the cell attachment factor to cause the different reactive group to covalently bind the chemical linking moiety to the molecules; and activating the photochemically reactive group of the chemical linking moiety in the presence of the solid surface of the device to cause the photochemically reactive group to covalently bind to the solid surface and to bind the molecules of the cell attachment factor to the solid surface in a sufficient population density of molecules to effectively shield the solid surface and to provide a biocompatible effective surface.

15. A method of providing a device with an effective biocompatible surface of an antithrombogenic agent capable of existing in contact with biological fluid or tissue of a living organism with a net beneficial effect on the organism, the method employing a solid surface of the device, molecules of the antithrombogenic agent and a chemical linking moiety possessing a photochemically reactive group capable upon activation of covalently bonding to the solid surface, and possessing a different reactive bonding to the solid surface, to the molecules of the antithrombogenic agent, one of the groups being unresponsive to a stimulus to which the other group responds, the method comprising:

activating the different reactive group of the chemical linking moiety in the presence of the molecules of the antithrombogenic agent to cause the different reactive group to covalently bind the chemical linking moiety to the molecules; and activating the photochemically reactive group of the chemical linking moiety in the presence of the solid surface of the device to cause the photochemically reactive group to covalently bind to the solid surface and to bind the molecules of the antithrombogenic agent to the solid surface in a sufficient population density of molecules to effectively shield the solid surface and to provide a biocompatible effective surface.

* * * * *